United States Patent [19]
Papapoulos et al.

[11] Patent Number: 5,885,973
[45] Date of Patent: Mar. 23, 1999

[54] BONE MASS ANABOLIC COMPOSITION COMPRISING OLPADRONATE

[75] Inventors: Socrates Papapoulos, Leiden, Netherlands; Jose Luis Ferretti, Rosario, Argentina; Rafael A. Labriola, Pilar, Argentina; Nelida Mondelo, Buenos Aires, Argentina; Emilio J.A. Roldan, Buenos Aires, Argentina

[73] Assignees: Gador, S.A., Argentina; University of Leiden, Netherlands

[21] Appl. No.: 875,202

[22] PCT Filed: Dec. 27, 1995

[86] PCT No.: PCT/EP95/05142

§ 371 Date: Oct. 10, 1997

§ 102(e) Date: Oct. 10, 1997

[87] PCT Pub. No.: WO96/19998

PCT Pub. Date: Jul. 4, 1996

[51] Int. Cl.$^6$ ........................................................ A61K 31/66
[52] U.S. Cl. ............................................. 514/106; 514/102
[58] Field of Search ........................................ 514/102, 106

[56] References Cited

U.S. PATENT DOCUMENTS 5,366,965  11/1994  Strein ........................................ 514/102

Primary Examiner—Theodore J. Criares
Attorney, Agent, or Firm—Pendorf & Cutliff

[57] ABSTRACT

The present invention provides methods for bone mass anabolic preservation or augmentation in human or other animal subjects affected by osteoporosis or other metabolic bone disorder characterized by systemic or regional bone loss, using bisphosphonates formulations, wherein the bone mass anabolic composition contains effective non-toxic doses of [3-(N,N-dimethylamine)-1-hydroxypropylidene]-bisphosphonic acid or olpadronate or the monosodium or other pharmaceutically acceptable salt thereof.

16 Claims, 3 Drawing Sheets

Spine bone mineral density in ox rats treated with compound (III)

Whole femur mineral density in ox rats treated with compound(III)

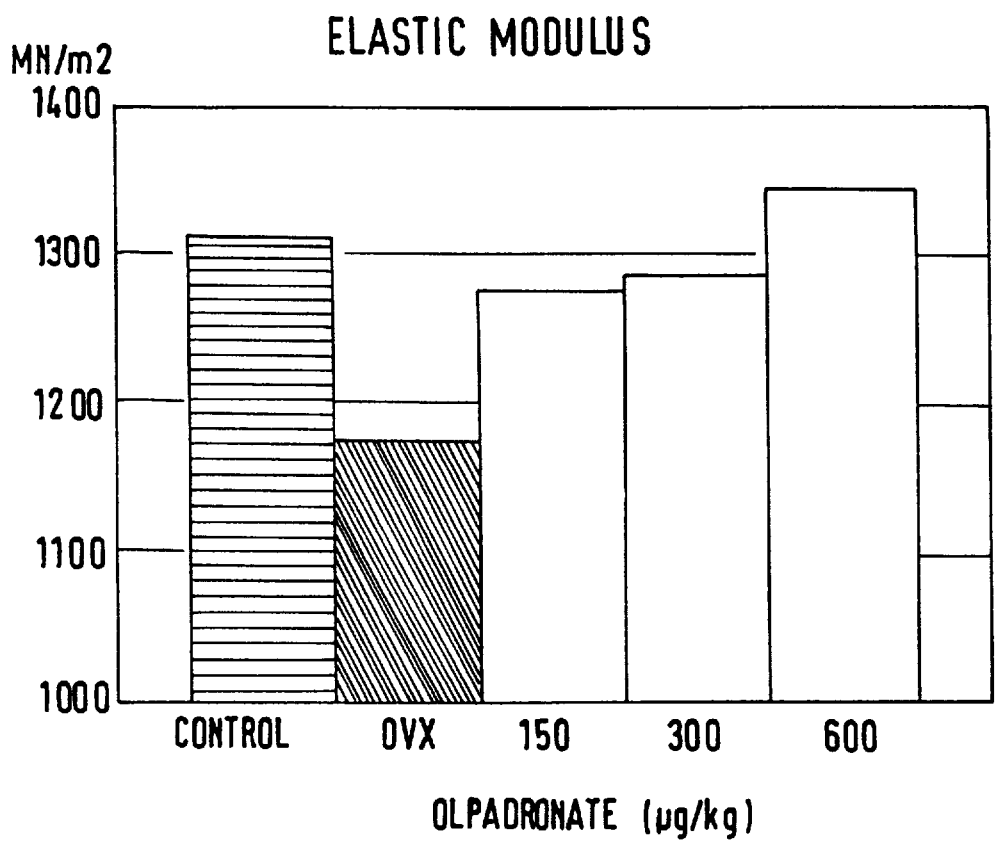

BONE MASS ANABOLIC COMPOSITION COMPRISING OLPADRONATE

This application is a 371 of PCT/EP95/05142 filed 28, Dec. 1994

BACKGROUND OF THE INVENTION

1. Field of the Invention

Bisphosphonates, also known as diphosphonates, are synthetic analogues of pyrophosphate characterized by two carbon-phosphate bonds and a high affinity for mineralized tissues. The substitution of the oxygen atom in the pyrophosphate molecules (P-O-P) by a carbon in the bisphosphonate molecules (P-C-P) made the latter compounds resistant to biological degradation and suitable for clinical use. Bisphosphonates were originally developed as inhibitors of calcium crystal growth and they were found to suppress osteoclast-mediated bone resorption. They were subsequently used for the treatment of acute and chronic conditions characterized by increased bone resorption and/or accelerated bone loss as osteoporosis.

2. Description of the Related Art

However, long term bone resorption inhibition may affect the bone remodeling process, and in consequence bone quality, resulting in bad biomechanical performance and subsequent increased risk of fracture.

It was further found that the presence of a nitrogen molecule in the side chain of the bisphosphonate structure increases its potency and specificity toward bone resorption.

The use of bisphosphonates in the treatment of bone metabolic disorders is known in principle, such as methods to interact with abnormal deposition and dissolution of difficultly soluble calcium salts or as bone resorption inhibition. U.S. Pat. No. 3,962,432 discloses the use of aminoalkane-diphosphonic acids for the treatment of a variety of calcium disorders. U.S. Pat. No. 4,711,880 discloses crystalline disodium 3-amino-1-hydroxypropane-1,1-diphosphonate pentahydrate for oral treatment of disorders of the calcium and phosphate metabolism. U.S. Pat. No. 5,137,880 dicloses bicyclic diphosphonate compounds, pharmaceutical preparations, and methods for treating abnormal calcium and phosphate metabolism. U.S. Pat. No. 5,205,253 discloses diphosphonic acid derivatives, processes for their production and pharmaceutical preparations containing these compounds for the treatment of calcium metabolism. PCT/WO93/11786 discloses a method for the treatment of osteoporosis using bisphosphonates and parathyroid hormone. PCT/WO93/11774 discloses the treatment of periodontal disease with alendronate.

The use of olpadronate and its derivatives as inhibitors of calcium crystal growth is also known in principle. U.S. Pat. No. 4,054,598 discloses a method with sequestering agents, especially for alkaline earth metal ions, having the formula 1-hydroxy-3-amino-alkane-1,1-diphosphonic acids, useful for the treatment of disturbances of the calcium or phosphate metabolism characterized by abnormal deposition of difficultly soluble calcium salts or the abnormal dissolution of hard tissues causing losses of hard bone substance, which cannot be replaced or only by incompletely crystallized tissues, such as Paget's disease, lithiasis, arthritis and others. Spanish Pat. No. P9100885 (Pub. No. ES-A-2034877) discloses pharmaceutical liposome preparations containing bisphosphonates as active compounds.

An effect different from bone resorption inhibition has been searched and anabolic phases has been added to cyclical bisphosphonate treatment (Eur Pat. No. A-162510).

It has now been discovered by the inventors hereof that olpadronate, obtained by a synthesis process herein described (previously known from Argentine Pat. No. 200,473 that discloses a process for the preparation of 1-hydroxyalkyliden-diphosphonic acids and its salts, extended to Argentine Pat. No. 218,558 that discloses a process to prepare 3-amino-1-hydroxy-propylidene-diphosphonic acid and their salts), displays an original anabolic mechanism of action preserving and augmenting bone mass, at non-toxic doses with no irritation of the gastrointestinal tract even in high doses.

SUMMARY OF THE INVENTION

Accordingly, the invention refers to olpadronate compositions and combinations as a new anabolic and non-toxic medicament to prevent or to treat bone mass loss conditions, such as all forms of osteoporosis, prolonged bed-rest, arthritis, hyperparathyroidism, and periodontal disease.

According to the present invention, there is provided a novel use of an effective non-toxic amount of [3-(N,N-dimethylamino)-1-hydroxypropylidene]-bisphosphonic acid or olpadronate (WHO generic name) or the monosodium or other pharmaceutically acceptable salt thereof for the preparation of a medicament for anabolic preservation and augmentation of bone mass. Such efforts are related to an improvement of biomechanical properties of bone in human or other animal subjects already affected by bone mass loss.

In addition, the claimed invention may be used in combination with one calcium salt, vitamin D or derivates thereof, fluoride salt, androgen and/or estrogen supplements.

Olpadronate may also be used in oral formulations or intravenously with or without a pharmaceutically acceptable carrier, diluent or vehicle.

Preferably the oral dosis of olpadronate (or its salt) is in the range of 1 to 15 mg/day of [3-(N,N-dimethylamino)-1-hydroxypropylidene]-bisphosphonic acid or the monosodium or other pharmaceutically acceptable salt thereof.

Alternatively, the intravenous dosis of olpadronate (or its salt) is in the range of 0.15 to 0.2 mg/kg/day of [3-(N,N-dimethylamino)-1-hydroxypropylidene]-bisphosphonic acid or the monosodium or other pharmaceutically acceptable salt thereof.

BRIEF DESCRIPTION OF THE DRAWINGS

FIG. 3 presents data showing bone material quality (elastic modulus and maximum elastic stress) of ovariectomy reduced bone material non-treated and and compound (III) treated animals.

DETAILED DESCRIPTION OF THE INVENTION

Example 1

Figure 1:
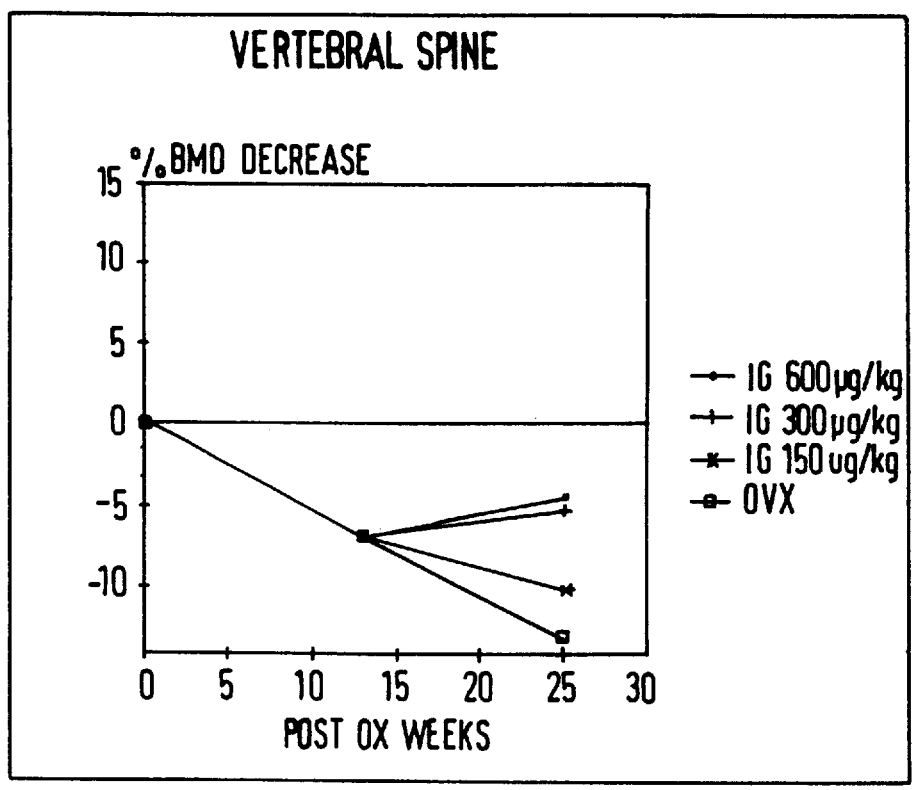
FIG. 1 is a plot of BMD % mean decrease in ovariectomized and hemiciaticectomized female ox rats treated with various levels of compound (III) in comparison with operated non-treated animals.

Olpadronate synthesis:

a. Preparation of 3-(N,N-dimethylamino)-propionic acid (I).

Transfer 153 l hydrochloric acid and 30 l 3-(N,N-dimethylamino)-propionitrile to a 250 l reactor. Stir during 3 hours, cool and filter. Concentrate the filtrate with reduced pressure until half its original volume is obtained. Add 40 l isopropanol and cool. Filter the suspension with reduced pressure and wash with isopropanol. Dry until constant weight. 41.3 kg 3-(N,N-dimethylamino)-propionic acid with m.p. 188°–192° C. is obtained.

b. Preparation of [3-(N,N-dimethylamino)-1-hydroxypropylidene]-bisphosphonic acid (II).

Transfer 2 kg of (I) to a 22 l reactor. Add 0.94 l of water and then slowly, with constant stirring, 2.3 l phosphorus trichloride. After this addition, the mixture is left with stirring during one hour. Add slowly with stirring 0.99 l phosphorus oxychloride and then 2 l water. Filter with reduced pressure and wash the solid with methanol. Dry in an oven with forced air circulation until the solid is dry. 1.3 kg of (II) is obtained.

c. Preparation of [3-(N,N-dimethylamino)-1-hydroxypropylidene]-bisphosphonic acid monosodium salt (III).

Add with constant stirring 11,11 kg of (II) to 33.3 l sodium hydroxide (50,7 g/l). Filter if necessary, add 122 l of methanol and dry in an oven with forced air circulation until constant weight. 10.7 kg of (III) is obtained.

Example 2

In vivo testing of the anabolic effect

Compound (III) was given in doses between 5 and 50 mg/day orally to patients with vertebral osteoporosis and an age range between 2 and 70 years. In the adult patients, increases in bone mass up to 13% of initial values were observed during 3 years follow-up. In the children, not only increases of bone mass were obtained, but there was also radiological evidence of augmentation of cortical and trabecular bone.

Example 3

In vivo testing of bone mass augmentation in intact rats.

Male and female Wistar intact rats (with normal bone mass) were treated with oral compound (III) 8, 40 and 200 mg/kg/d for 6 months. Femora were dissected and bone mineral content (BMC) and total bone area (TBA) were measured by a specially-programmed Norland X-ray densitometer. Bone mineral density (BMD) was determined as the BMC/TBA ratio. There were significant increases in the BMD of the treated groups ranging between 39 to 67%.

Example 4

In vivo testing of bone mass preservation in osteopenic rats.

Prevention of bone loss induced by ovariectomy (ox) and unilateral sciaticectomy (cx) in female rats or by unilateral sciaticectomy in male rats was studied using various modes (cyclical, continuous) and routes of administration of compound (III).

a. Oral compound (III) or monosodium salt of pamidronate were given to female Wistar rats immediately after the operation for 11 weeks. Bone mass (BMD) was assessed as described above. In ox/cx animals there was a decrease in BMD, the magnitude of which depended on the site and side measured. (III) prevented bone loss in femora and vertebra dose-dependently being 5 to 10 times more potent than monosodium salt of pamidronate.

b. Intravenous compound (III) given at different doses every 15 days after the operation for 12 weeks to female control or ox/cx rats. The doses used were 75, 150 and 300 μg/kg. In this study bone loss in control group reached up to 19.1% left (cx) and 8.6% in right femora. The three dose levels of i.v. olpadronate were able to prevent cortical as trabecular bone loss. While BMD loss in control's vertebral bodies was about 11.8%, treated animals not only did show maintenance, but also showed an increase from 4.7 to 8.6%. Whole body mineral density decreased 5.2% in the control group. It could be prevented only in the two higher treated dose groups.

c. Intravenous compound (III) or monosodium salt of pamidronate were given to 3-month old male control of cx rats after the operation for 3 months. Treated with intravenous repeated doses of compound (III), 0.5, 0.25 and 0.125 mg/kg body weight compared with monosodium salt of pamidronate 5, 2.5 and 1.25 mg/kg body weight. Doses were selected according to previous results observed with monosodium salt of pamidronate and its equivalence with. Each dose was diluted to administrate similar volume (2 ml/kg) in each animal. A total of 7 injections were administered each 15 days. Operated non treated groups of rats served as controls.

Immobilized leg showed 9% less bone mass in its femur than contralateral femur, assessed through densitometric techniques (Dual photonic densitometer Norland XR-26 with a software adapted to small animals). Both bisphosphonates prevented bone loss with all administered dose levels.

d. Regional bone loss (proximal and distal femur and midshaft) was greater at distal femur (17%). Bone mineralization gain was significantly increased with both bisphosphonates. Midshaft femora (cortical tissue predominance) mineralization loss was 6% in controls. All compound (III) doses were effective to prevent osteopenia, while monosodium salt of pamidronate was partially effective in this region. Compound (III) dose levels were 10 fold lower. This model of disuse osteopenia in rats demonstrates superiority with regards to compact bone at much lower doses than monosodium salt of pamidronate.

Example 5

In vivo testing of bone mass augmentation in osteopenic rats.

The effects of cyclical administrations of I.V. compound (III) to osteopenic rats were evaluated in order to elucidate if the compound was able to restore bone mineralization density in animals previously subjected to bone loss.

Figure 2:
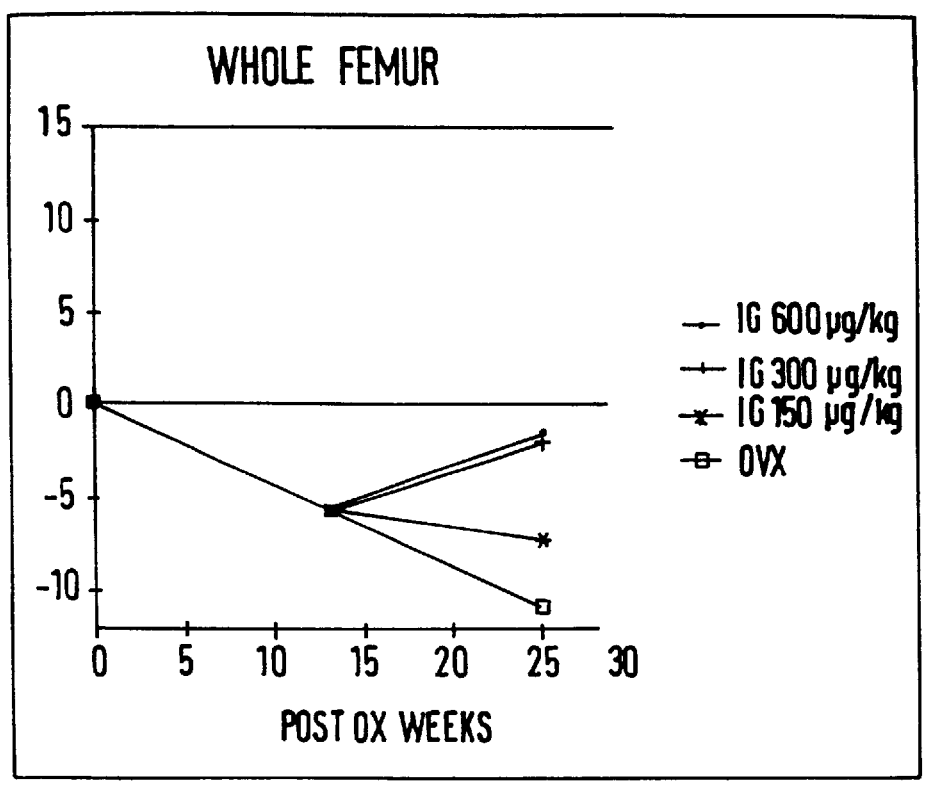
FIG. 2 shows isolated whole femur mineral density data for the experiment of FIG. 1.

Female rats, 2.5 months old, n 6-8 each group, were ovariectomized and hemiciaticectomized according to previous experiments. The animals were housed during 13 weeks after surgery and then compound (III) was administered in 150, 300 or 600 μg, intravenously, each 15 days during the following 12 weeks. An operated non-treated group and intact animals served as controls. Spine and femur BMD was assessed by densitometry as in previous experiments. Spine of non-treated animals showed a mean BMD decrease of 12.9% in comparison with non-operated rats. Instead BMD % mean decrease was of −9.3, −4.3 and −3.6% in compound (III) treated groups (FIG. 1). The last two values correspond to the higher doses, which were found non-significant vs non-operated rats. Statistical results were similar in isolated whole femur (FIG. 2). BMD % mean loss was −10.4, −6.7, −1.5, and −0.7 respectively in 0, 150, 300 and 600 μg IG-8801 groups, compared to non-operated rats. In proximal femur the higher dose compound (III) treated group showed an increase of 5.0% BMD with respect to intact animals. In mid femur the two higher dose groups showed increased values (+0.8 and +3.2%) and in distal femur mean BMD loss was of −11.4, −7.9, −3.6 and −5.0, respectively, in 0, 150, 300 and 600 μg (III) groups. For further details, see FIG. 1 and 2, showing "Spine bone mineral density in ox rats treated with compound (III)" and "Whole femur mineral density in ox rats treated with compound (III)", respectively.

It is concluded that this model induces bone loss in spine and femur that can be restored with (III). Effective doses in this model are 300 and 600 μg.

Biomechanical tests were performed in femur diaphyses in order to verify the bone mechanical performance of the anabolic restored bone. Ovariectomy reduced bone material quality (elastic modulus and maximum elastic stress), and the fracture load without affecting their stiffness or cross-sectional moment of inertia. Compound (III) reverted all the negative effects of ovariectomy and enhance diaphyseal stiffness to overnormal without affecting bone geometry (FIG. 3).

Example 6
Oral lethality and chronic toxicity test:

In rats the LD50 of compound (III) was estimated between 1800 and 2300 mg/kg, the LD50 in mice was 1400 mg/kg.

Three groups of rats (N=50 ♂ and 50 ♀) were treated with daily oral doses of 8 mg, 40 mg, and 200 mg/kg for 6 months. A fourth group served as control.

Some of the animals (5 out of 30) in the higher dose group died in hypocalcaemia. Male rats were more affected than female, and the whole 200 mg/kg group suffered teeth fracture.

No hematological or urine significant changes were detected in treated animals. Serum GOT and GPT increased without showing a clear relationship with dose or administration term.

Relative and absolute weight of liver decreased in treated animals, while a significant increase in femora weight was measured. Bone marrow in 200 and 40 mg/kg treated animals showed a slight decrease in megacaryocyte population. No other relevant change was observed. Both doses of 8 and 40 mg/kg were qualified as active, in view of femora weight and BMD increase.

These results indicate that dental structures and calcium levels are only adversely affected by the highest dose (200 mg/kg).

In conclusion, toxicity of some organs is described with doses 50 to 200 fold higher than the proposed highest human doses.

Example 7
Intravenous lethality and chronic toxicity test:

In rats the LD50 of compound (III) was 117 mg/kg and in mice 109 mg/kg. The differences between oral and intravenous doses is due to poor absorption of the orally administered bisphosphonate.

Animals exhibited convulsion, dyspnea and hindlimb paralysis, symptoms which can be attributed to severe hypocalcaemia due to the primary action of the drug.

A four-week, daily administered, intravenous compound (III) test was carried out in 200 Wistar male and female rats. Selected doses were 0 (saline solution ), 0.5, 2.5, 10 and 12.5 mg/kg. Twenty animals per sex per dose level were randomized. Two additional groups treated with the two higher doses were observed to assess reversibility of toxic effects.

Animals were injected intravenously with adjusted concentrations of compound (III) in order to receive 2 ml/kg body weight. The two additional groups were followed during a second period free of treatment of 4 weeks more.

Toxic manifestations were limited to the two mentioned high (10 mg/kg and 12,5 mg/kg) dose treated groups. No toxicity signs neither mortality were detected in controls and the two low dose (0.5 and 2.5 mg/kg) groups. With the higher dose local signs were observed in the site of injections, edema erythema and necrosis. This manifestations began at day 7 and were more evident in male rats. This fact provoked the affected animals to receive a minor number of injections along the period of the study.

Animals of the high dose group were upset, scary and irritable after dosing. Four rats died (one male and three females of the high dose group) during the active treatment period and two more died (one male and one female of the high dose group) during the recovery period. Rats of the high group showed a mild diminution of water consumption as well as the body weight gain. After stopping treatment, rats of the two additional groups recover body weight gain.

Urinalysis showed glycosuria and granulated or leukocytic cylinders in scant number of male animals of the high dose group. Low hematocrit values, leukocytosis and anisocytosis were observed in males and females of the high dose group. Decreased creatinine clearance, and augmented BUN and serum creatinine were seen in some animals of the high dose level. Gross examination of organs showed increased spleen and ganglions sizes (infarction), and gonadal alterations in one third of the high dose treated animals. Histological examinations reveal glomerulonephritis, tubular necrosis, interstitial nephritis (in 4 rats), epithelial atrophy and tubular dilation in testis (1 rat) and myocardial stroke (1 rat). All mentioned findings seem reversible with the exceptions of the anisocytosis and gonadal alterations. Low doses, 0.5 and 2.5 mg/kg groups did not register abnormalities.

In conclusion, toxicity of some organs is described with dose proportional to 100 times the proposed highest human doses.

What is claimed is:

1. A method for improving bone material quality in human subjects where bone material quality is impaired, said method comprising administering to said human subjects in need thereof an effective amount of a (3-[N,N,-dimethylamino]-1-hydroxypropylidene)-bisphosphonic acid of the formula:

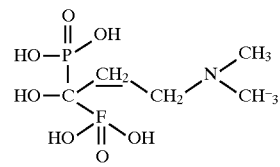

or pharmaceutically acceptable salt thereof, orally in an amount in the range of 1 to 15 mg/day or via IV in the range of 0.025 to 0.20 mg/kg application based on a twice monthly application.

2. A method as in claim 1, further comprising the simultaneous or sequential administration of at least one calcium salt.

3. A method as in claim 1, further comprising the simultaneous or sequential administration of vitamin D or derivatives thereof.

4. A method as in claim 1, further comprising the simultaneous or sequential administration of at least one fluoride salt.

5. A method as in claim 1, further comprising the simultaneous or sequential administration of at least one androgen.

6. A method as in claim 1, further comprising the simultaneous or sequential administration of at least one estrogen.

7. A method as in claim 1, wherein said (3-[N,N,-dimethylamino]-1-hydroxypropylidene)-bisphosphonic acid is administered in the form of a pharmaceutical composition comprising a pharmaceutically acceptable carrier, dilutant or vehicle.

8. A method as in claim 1, wherein the dosis of said (3-[N,N,-dimethylamino]-1-hydroxypropylidene)-bisphosphonic acid or the monosodium or other pharmaceutically acceptable salt thereof is in the range of 0.025 to 0.15 mg/kg/application based on a twice monthly application.

9. A method for bone mass anabolic preservation or augmentation in subjects affected by osteoporosis or other metabolic bone disorder characterized by systemic or regional bone loss, said method comprising administering to said subjects in need thereof an effective amount of a (3-[N,N,-dimethylamino]-1-hydroxypropylidene)-bisehosphonic acid of the formula:

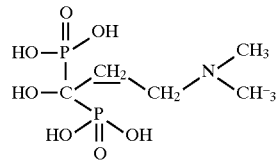

or pharmaceutically acceptable salt thereof, orally in an amount in the range of 1 to 15 mg/day or via IV in the range of 0.025 to 0.20 mg/kg/application based on a twice monthly application.

10. A method as in claim 9, further comprising the simultaneous or sequential administration of at least one calcium salt.

11. A method as in claim 9, further comprising the simultaneous or sequential administration of vitamin D or derivatives thereof.

12. A method as in claim 9, further comprising the simultaneous or sequential administration of at least one fluoride salt.

13. A method as in claim 9, further comprising the simultaneous or sequential administration of at least one androgen.

14. A method as in claim 9, further comprising the simultaneous or sequential administration of at least one estrogen.

15. A method as in claim 9, wherein said (3-[N,N,-dimethylamino]-1-hydroxropylidene)-bisphosphonic acid is administered in the form of a pharmaceutical composition comprising a pharmaceutically acceptable carrier, diluent or vehicle.

16. A method as in claim 9, wherein the dosis of said (3-[N,N,-dimetzhlatmino]-1-hydroxypropylidene)-bisphoeshonic acid or the monosodium or other pharmaceutically acceptable salt thereof is in the range of 0.025 to 0.15 mg/kg/application based on a twice monthly application.

* * * * *